(12) United States Patent
Eliyahu et al.

(10) Patent No.: US 11,173,287 B2
(45) Date of Patent: Nov. 16, 2021

(54) ADJUSTABLE BALLOON FIXATION FOR A SHEATH

(71) Applicant: Biosense Webster (Israel) Ltd., Yokneam (IL)

(72) Inventors: Shiran Eliyahu, Yokneam Illit (IL); Alaa Zoubi, Sakhnin (IL); Assaf Pressman, Pardes Hanna-Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 133 days.

(21) Appl. No.: 16/237,056

(22) Filed: Dec. 31, 2018

(65) Prior Publication Data
US 2020/0206479 A1 Jul. 2, 2020

(51) Int. Cl.
| | |
|---|---|
| *A61M 25/10* | (2013.01) |
| *A61M 25/00* | (2006.01) |
| *A61B 1/00* | (2006.01) |
| *A61B 17/00* | (2006.01) |

(52) U.S. Cl.
CPC ........ *A61M 25/10* (2013.01); *A61M 25/0023* (2013.01); *A61B 1/00082* (2013.01); *A61B 1/00147* (2013.01); *A61B 2017/00557* (2013.01); *A61M 2025/0024* (2013.01); *A61M 2025/1081* (2013.01)

(58) Field of Classification Search
CPC .............. A61M 25/10; A61M 25/0023; A61M 2025/1081; A61B 1/00147; A61B 2017/00557
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,558,091 A | 9/1996 | Acker et al. | |
| 5,882,334 A * | 3/1999 | Sepetka | A61M 25/01 604/164.08 |
| 5,944,022 A | 8/1999 | Nardella et al. | |

(Continued)

FOREIGN PATENT DOCUMENTS

CN 201197843 Y 2/2009

OTHER PUBLICATIONS

Extended European Search Report dated Jun. 4, 2020 for European Patent Application No. 19220178.8.

*Primary Examiner* — Bradley J Osinski
(74) *Attorney, Agent, or Firm* — Volpe Koenig

(57) ABSTRACT

A tool positioning system for use in a medical procedure is provided which includes a medical tool configured to be navigated to a target tool location within a portion of an organ of a patient. The medical tool includes a sheath having a tube defined by a sheath wall, the sheath extending a length in a proximal-distal direction and an inflatable balloon coupled to the sheath and configured to move along the length of the sheath in the proximal-distal direction. When the inflatable balloon is inflated at a target balloon location along the length of the sheath, the inflated balloon is fixed at the target balloon location. The tool positioning system also includes memory configured to store location of the tool in a three dimensional (3D) space and at least one processor configured to generate mapping information for displaying locations of the tool in the 3D space.

3 Claims, 10 Drawing Sheets

(56) References Cited

U.S. PATENT DOCUMENTS

| | | |
|---|---|---|
| 5,983,126 A | 11/1999 | Wittkampf |
| 6,172,499 B1 | 1/2001 | Ashe |
| 6,177,792 B1 | 1/2001 | Govari et al. |
| 6,266,551 B1 | 7/2001 | Osadchy et al. |
| 6,456,828 B1 | 9/2002 | Ozluturk |
| 6,595,989 B1 | 7/2003 | Schaer |
| 6,690,963 B2 | 2/2004 | Ben-Haim et al. |
| 6,788,967 B2 | 9/2004 | Ben-Haim et al. |
| 7,340,288 B1 | 3/2008 | Karicherla et al. |
| 2006/0079845 A1 | 4/2006 | Howard et al. |
| 2007/0078386 A1 | 4/2007 | Salazar |
| 2008/0215008 A1 | 9/2008 | Nance et al. |
| 2009/0093806 A1 | 4/2009 | Govari et al. |
| 2009/0138007 A1 | 5/2009 | Govari et al. |
| 2012/0046666 A1 | 2/2012 | Klein |
| 2018/0185104 A1 | 7/2018 | Olson et al. |

\* cited by examiner

ADJUSTABLE BALLOON FIXATION FOR A SHEATH

SUMMARY

A tool positioning method is provided which includes positioning a medical tool, comprising a sheath and an inflatable balloon coupled to the sheath, at a target tool location within a portion of an organ of a patient. The method also includes moving the inflatable balloon in a proximal-distal direction along a length of the sheath to a target balloon location and inflating the inflatable balloon when the balloon is positioned at the target balloon location along the length of the sheath. The method further includes fixing the inflated balloon at the target balloon location along the length of the sheath to prevent the medical tool from moving from the target tool location.

A medical tool for use in a medical procedure is provided which includes a sheath having a tube defined by a sheath wall. The sheath extends a length in a proximal-distal direction. The medical tool also includes an inflatable balloon coupled to the sheath and a balloon-moving mechanism, coupled to the inflatable balloon. The balloon-moving mechanism is configured to move the inflatable balloon to different balloon locations along the length of the sheath. The medical tool also includes a balloon-fixing mechanism configured to fix the inflatable balloon, when inflated, to a target balloon location along the length of the sheath to prevent the medical tool from moving from a target tool location within a portion of an organ of a patient.

A tool positioning system for use in a medical procedure is provided which includes a medical tool configured to be navigated to a target tool location within a portion of an organ of a patient. The medical tool includes a sheath having a tube defined by a sheath wall, the sheath extending a length in a proximal-distal direction and an inflatable balloon coupled to the sheath and configured to move along the length of the sheath in the proximal-distal direction. When the inflatable balloon is inflated at a target balloon location along the length of the sheath, the inflated balloon is fixed at the target balloon location. The tool positioning system also includes memory configured to store location of the tool in a three dimensional (3D) space and at least one processor configured to generate mapping information for displaying locations of the tool in the 3D space.

These and other objects, features and advantages will be apparent from the following detailed description of illustrative embodiments thereof, which is to be read in connection with the accompanying drawings.

BRIEF DESCRIPTION OF THE DRAWINGS

A more detailed understanding can be had from the following description, given by way of example in conjunction with the accompanying drawings wherein.

DETAILED DESCRIPTION

Figure 1:
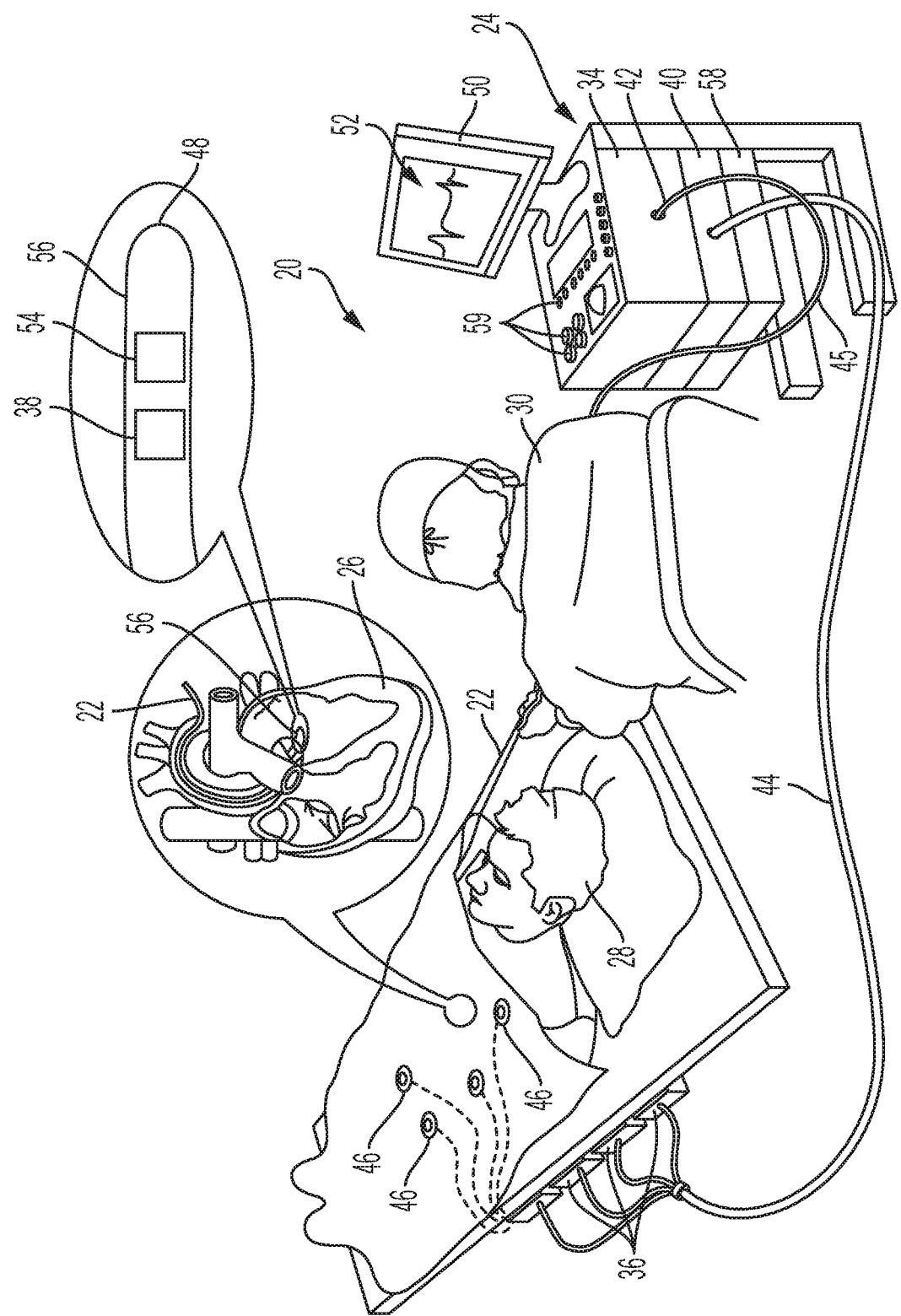
FIG. 1 is an illustration of an example medical system for navigating a tool in a 3-D space within which embodiments disclosed herein may be implemented.

A sheath may be used in intravascular, intracardiac or any intraluminal invasive medical procedures. For example, a sheath may be a tool, or part of a tool, of an electromagnetic navigation system used to determine the location of the sheath in a 3-D space during a medical procedure. This sheath allows devices (such as catheters, guide wires and needles, etc.) to pass through the sheath as well as suctioning in specific locations of a patient's anatomy. The sheath facilitates navigation through the patient's anatomy, curving the devices passing through it in a determined direction and maintaining desired balance between rigidity and flexibility (and force in some cases) to direct, stabilize and use the devices in specific locations in the body of the patient.

When positioning the sheath at a target location of a patient (e.g., in a heart) during a medical procedure, the sheath typically passes through a puncture hole or an existing fossa (i.e. a trans-septal puncture). During the procedure the location of the sheath serves as an access point to the target location.

In some situations, after the sheath is positioned at a target location, the sheath may move (e.g., slips) from its target location, requiring regaining access to the target location and/or repositioning of the sheath. For example, when the sheath is positioned (e.g., by a cardiac physician) into the right atrium, the sheath enters the left atrium through the fossa ovalis in the septum. The fossa ovalis is a depression in the tissue of the septum, which is used as a marker to indicate to the physician a location where the sheath can be inserted from the right atrium through the septum into the left atrium. When the sheath enters the left atrium, the sheath can slip back into the right atrium, causing a loss of access to the sheath. Regaining access to the sheath and/or repositioning of the sheath, however, is time consuming and poses additional risk for the patient (e.g., risk of injury).

Embodiments disclosed herein provide an apparatus and method of using a medical tool with an inflatable balloon to position a portion (e.g., a sheath) of the medical tool at a target tool location (e.g., location suitable for organ size and anatomy) inside an organ (e.g., the left atrium) of a patient's anatomy and securing the portion of the tool at the target tool location by inflating the balloon at the target location to prevent or limit movement of the tool at the target location in the organ.

Embodiments disclosed herein provide systems, tools and methods for adjusting the location of a balloon on a tool (e.g., on the sheath of the tool) and fixing (e.g., locking) the inflatable balloon at the location on the tool.

Embodiments disclosed herein provide a sheath, which may be a tool or part of a tool, of a medical system used to generate and display information (e.g., a chart, anatomical models of a portion of a patient and signal information). In some embodiments, the medical system may be an electromagnetic navigation system used to determine the location of the tool and/or sheath in a 3-D space during a medical procedure. During these medical procedures, medical tools generate and transmit signals (e.g., electrical signals based on the amplitude and phase of magnetic fields) to facilitate the determination of their locations.

FIG. 1 is an illustration of an example medical system 20 which may be used to generate and display information 52 (e.g., a chart, anatomical models of a portion of a patient and signal information). The system 20 and the tool 22 shown in FIG. 1 are merely by example. Medical tools, such as tool 22, can be any tool used for diagnostic or therapeutic treatment, such as for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, sheaths, probes, catheters, cutting tools and suction devices.

An operator 30 may insert the tool 22 into a portion of patient anatomy, such as the vascular system of the patient 28 so that a tip 56 of the tool 22 enters a chamber of the heart 26. The control console 24 may use magnetic position sensing to determine 3-D position coordinates of the tool (e.g., coordinates of the tip 56) inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 1), placed at known positions external to the patient 28, which are configured to generate magnetic fields in a predefined working volume that contains a portion of interest of the patient anatomy. Each of the emitting coils may be driven by a different frequency to emit a constant magnetic field. For example, in the example medical system 20 shown in FIG. 1, one or more emitter coils can be placed below the torso of the patient 28 and each configured to generate magnetic fields in a predefined working volume that contains the heart 26 of the patient.

As shown in FIG. 1, a magnetic field location sensor 38 is disposed at the tip 56 of tool 22. The magnetic field location sensor 38 generates electrical signals, based on the amplitude and phase of the magnetic fields, indicating the 3-D position coordinates of the tool (e.g., position coordinates of the tip 56). The electrical signals may be communicated to the control console 24 to determine the position coordinates of the tool. The electrical signals may be communicated to the control console 24 via wire 45.

Alternatively, or in addition to wired communication, the electrical signals may be wirelessly communicated to the control console 24, for example, via a wireless communication interface (not shown) at the tool 22 that may communicate with input/output (I/O) interface 42 in the control console 24. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions. The wireless digital interface and the I/O interface 42 may operate in accordance with any suitable wireless communication standard that is known in the art, such as for example, IR, RF, Bluetooth, one of the IEEE 802.11 family of standards (e.g., Wi-Fi), or the HiperLAN standard.

Although FIG. 1 shows a single magnetic field location sensor 38 disposed at the tip 56 of tool 22, tools may include one or more magnetic field location sensors each disposed at any tool portion. The magnetic field location sensor 38 may include one or more miniature coils (not shown). For example, a magnetic field location sensor may include multiple miniature coils oriented along different axes. Alternatively, the magnetic field location sensor may comprise either another type of magnetic sensor or position transducers of other types, such as impedance-based or ultrasonic location sensors.

The signal processor 40 is configured to process the signals to determine the position coordinates of the tool 22, including both location and orientation coordinates. The method of position sensing described hereinabove is implemented in the CARTO mapping system produced by Biosense Webster Inc., of Diamond Bar, Calif., and is described in detail in the patents and the patent applications cited herein.

The tool 22 may also include a force sensor 54 contained within the distal end 32. The force sensor 54 may measure a force applied by the tool 22 (e.g., the tip 56 of the tool) to the endocardial tissue of the heart 26 and generate a signal that is sent to the control console 24. The force sensor 54 may include a magnetic field transmitter and a receiver connected by a spring in the distal end 32, and may generate an indication of the force based on measuring a deflection of the spring. Further details of this sort of probe and force sensor are described in U.S. Patent Application Publications 2009/0093806 and 2009/0138007, whose disclosures are incorporated herein by reference. Alternatively, the distal end 32 may include another type of force sensor that may use, for example, fiber optics or impedance measurements.

The tool 22 may also include an electrode 48 coupled to the tip 56 and configured to function as an impedance-based position transducer. Additionally, or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

Although the example medical system 20 may be configured to measure the position of the tool 22 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558, 091, 6,172,499 6,177,792, the disclosures of which are incorporated herein by reference. Impedance-based position tracking techniques are described, for example, in U.S. Pat. Nos. 5,983,126, 6,456,828 and 5,944,022, the disclosures of which are incorporated herein by reference.

The I/O interface 42 may enable the control console 24 to interact with the tool 22, the body surface electrodes 46 and any other sensors (not shown). Based on the electrical impulses received from the body surface electrodes 46 and the electrical signals received from the tool 22 via the I/O interface 42 and other components of medical system 20, the signal processor 40 may determine the location of the tool in a 3-D space and generate the display information 52, which may be shown on a display 50.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example shown at FIG. 1, the control console 24 is connected, via cable 44, to body surface electrodes 46, each of which are attached to patient 28 using patches (e.g., indicated in FIG. 1 as circles around the electrodes 46) that adhere to the skin of the patient. Body surface electrodes 46 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in an article (e.g., a vest) disposed on the patient 28. During operation, the body surface electrodes 46 assist in providing a location of the tool (e.g., tool including an inflatable balloon) in 3-D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28. In addition to or alternative to wired communication, the body surface electrodes 46 may communicate with the control console 24 and one another via a wireless interface (not shown).

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 20 may include a second operator that manipulates the control console 24 while the operator 30 manipulates the tool 22. It should be noted that the configuration shown in FIG. 1 is exemplary. Any suitable configuration of the medical system 20 may be used and implemented.

Figure 2:
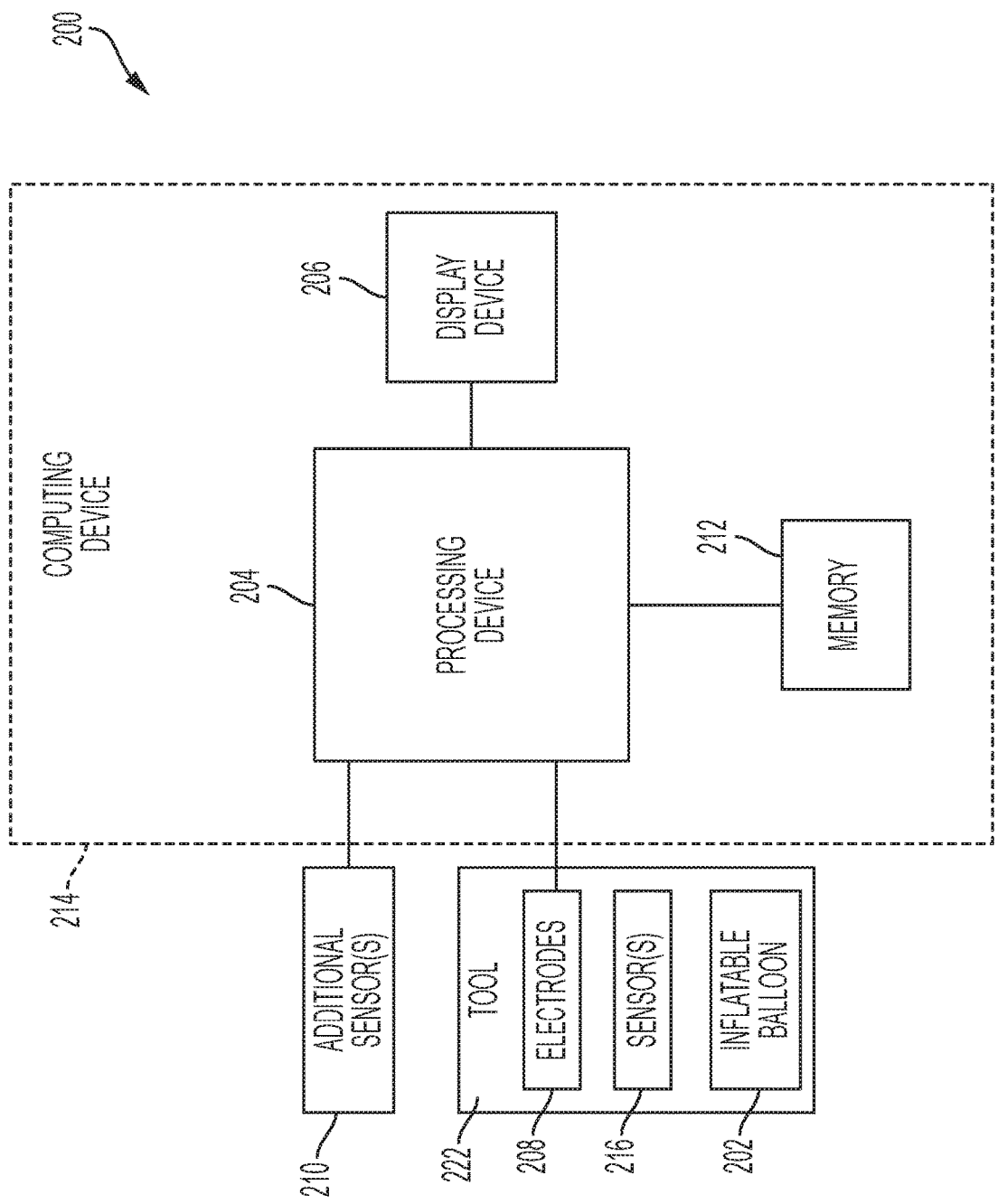
FIG. 2 is a block diagram illustrating components of an example medical system for use with embodiments described herein.

FIG. 2 is a block diagram illustrating example components of a medical system 200 for use with embodiments described herein. As shown in FIG. 2, the system 200 includes medical tool 222, processing device 204, display device 206 and memory 212. The processing device 204, display device 206 and memory 212 are a part of computing device 214. In some embodiments, the display device 206 may be separate from computing device 214. Computing device 214 may also include an I/O interface, such as I/O interface 42 shown in FIG. 1.

Tool 222 includes an array of electrodes 208 each configured to detect electrical activity (electrical signals) of an area of an organ (e.g., a heart) over time. When an ECG is performed, each electrode detects the electrical activity of an area of the organ in contact with the electrode. Tool 222 also includes a plurality of sensors 208. The sensors 208 include, for example, a magnetic field location sensor (e.g., sensor 38 in FIG. 1) for providing location signals to indicate the 3-D position coordinates of the tool 222. In some procedures, one or more additional sensors 210 that are separate from the tool 222, as shown in example system 200, are also used to provide location signals. Additional sensors 210 may also include sensors (e.g., electrodes on the skin of a patient) used to assist with detection of electrical activity of an organ via detection of electrical changes on the skin due to the electro-physiologic pattern of the organ, such as the heart. Tool 222 also includes an inflatable balloon 202, which may be adjusted and inflated at a target location in the organ of the patient to secure the tool 222 at the target location by preventing or limiting movement of the tool 222 at the target location, as described in more detail below.

Processing device 204 may include one or more processors each configured to process the ECG signals, record ECG signals over time, filter ECG signals, fractionate ECG signals into signal components (e.g., slopes, waves, complexes) and generate and combine ECG signal information for displaying the plurality of electrical signals on display device 206. Processing device 204 may also generate and interpolate mapping information for displaying 3D maps of the heart on display device 206. Processing device 204 may include one or more processors (e.g., signal processor 40) configured to process the location information acquired from sensors (e.g., additional sensors 210 and sensors 216) to determine the position coordinates of the tool 222, including both location and orientation coordinates.

In addition, processing device 204 determines locations of anatomical regions of an organ (e.g., the heart) on the map, determines which electrical signals correspond to areas of the organ that are located within the anatomical regions of the organ and generate signal information (e.g., correlated ECG information) for displaying electrical signals determined to correspond to the areas of the organ that are located within the anatomical regions of the organ (i.e., determined to be the electrical signals acquired by electrodes (i.e., poles) disposed at the corresponding areas of the organ). Processing device 204 drives display device 206 to display dynamic maps (i.e., spatio-temporal maps) of the organ and the electrical activity of the organ using the mapping information and the signal information. Processing device 204 also drives display device 206 to display the signals determined to be located within the anatomical region of the organ using the correlated signal information.

Display device 206 may include one or more displays each configured to display 3D maps of the organ representing spatio-temporal manifestations of the electrical activity of the organ over time and display the electrical signals acquired from the organ over time. For example, a 3D map of the organ representing the electrical activity of the organ for a specific time interval and the electrical signals acquired from the organ during the time interval may be displayed concurrently on the same display device. Alternatively, the 3D map of the organ and the electrical signals acquired during the same time interval may be displayed on separate display devices.

The electrodes 208, sensor(s) 216 and additional sensor(s) 210 may be in wired or wireless communication with processing device 204. Display device 206 may also be in wired or wireless communication with processing device 204.

Figure 3:
FIG. 3 is an illustration of an example medical tool, positioned within a portion of a heart, for use with embodiments described herein.

FIG. 3 is an illustration of an example medical tool, positioned within a portion of a heart, for use with embodiments described herein. In the example shown in FIG. 3, the medical tool 322 comprises a sheath 301 (comprising a shaft or tube) and an inflatable balloon 302 coupled (e.g., directly or indirectly connected) to the sheath 301. FIG. 3 illustrates the sheath 301 and the balloon 302 positioned in the left atrium 303 of the heart after having entered the left atrium 303 from the right atrium 304. The balloon 302 is shown in an inflated state inside the left atrium 303, providing stability by preventing the sheath 301 from moving (e.g., slipping back) into the right atrium 304.

Although the tool 322 is shown in a heart in FIG. 3, the use of the tool 322 in a heart is an example. The tool 322 may be used in other organs and other portions of a patient's anatomy. The location of the balloon 302 around the shaft of the sheath 301 shown in FIG. 3 is also an example. The balloon 302 is adjustable to different locations around the shaft of the sheath 301, suitable for different procedures, users and anatomies as well as sheath and catheter maneuvering strategies.

Figure 4:
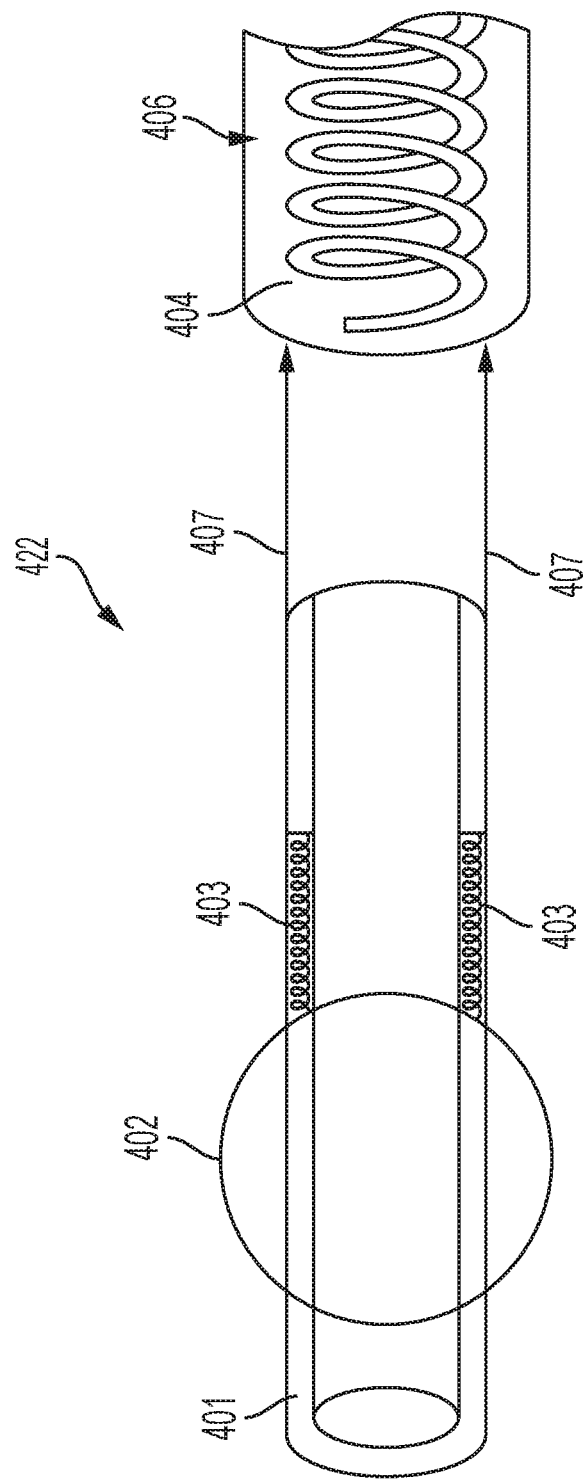
FIG. 4 is a diagram illustrating components of an example medical tool according to an embodiment.

FIG. 4 is a diagram illustrating components of tool 422 according to an embodiment. The tool 422 includes a sheath 401 and a rotatable handle 406 coupled to the sheath via wires 407. The sheath 401 includes an inflatable balloon 402 and spring elements 403, coupled to the balloon 402 in a wall of the sheath 401 and coupled to the wires 407. Spring elements 403 are configured to expand and contract to adjust the balloon 402 to different locations along the sheath 401. Each spring element 403 may include a helical spring. Spring elements may also include other types of spring-like mechanisms configured to adjust the balloon 402 to different locations along the sheath 401. In addition, sheaths may include any number of spring elements, including a single spring element, to adjust the balloon 402 to different locations along the sheath 401. Tools may include any number of wires, including a single wire, to adjust the balloon 402 to different locations along the sheath 401.

Rotatable handle 406 includes a screw element 404 disposed within the rotatable handle 406. The screw element 404 may, for example, be a screw having threads which are configured to rotatably engage with opposable threads of the sheath. Spring element 403, rotatable handle 406, screw element 404, and wires 407 together form a balloon moving mechanism, used to move the balloon 402 to different locations along the sheath 401. For example, the rotatable handle 406 is rotated about the screw element 404 to exert a force (e.g., push force or pull force depending on the rotational direction of the rotatable handle 406) on the wires 407, which causes the spring elements 403, which are coupled to the wires 407, to expand or contract. The expanding and contracting of the spring elements 403 causes the balloon 402, which are coupled to the spring elements 403, to move in opposing directions along the sheath 401.

Figure 5:
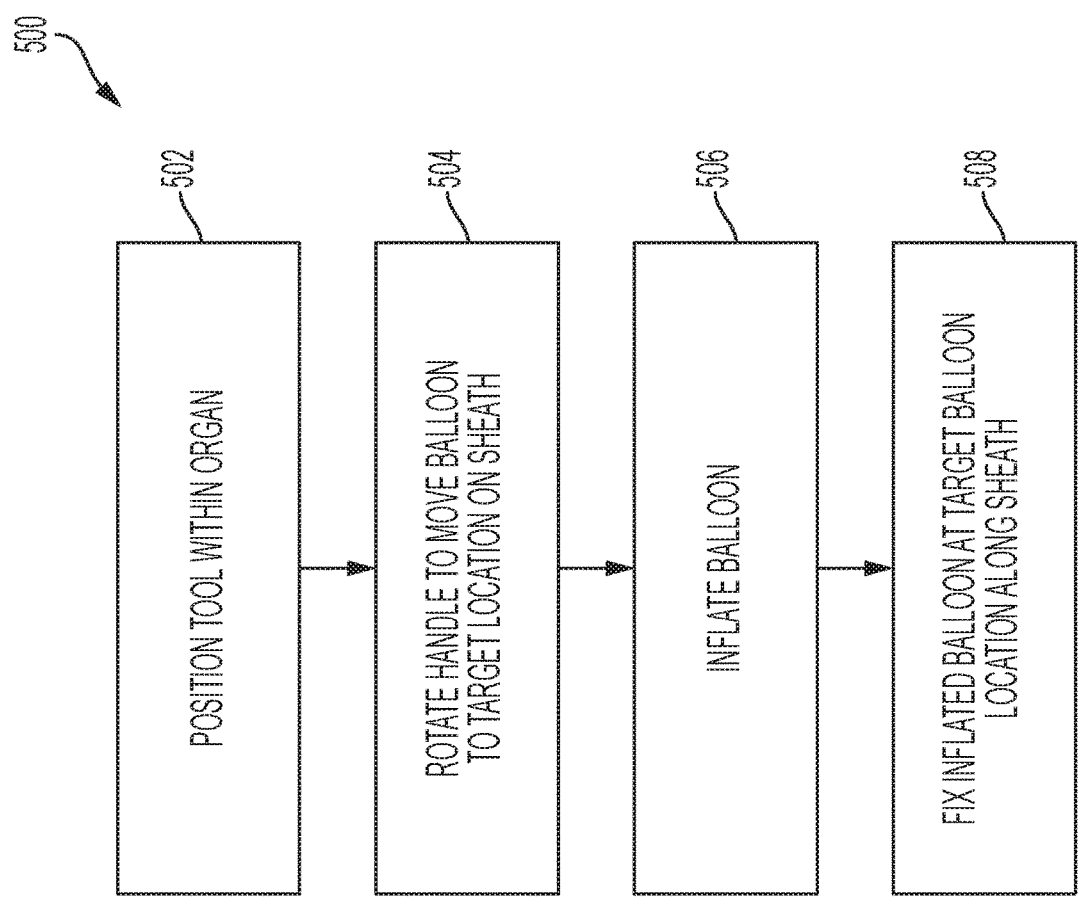
FIG. 5 is a flow diagram illustrating an example method of positioning the tool shown in FIG. 4 at a target location of a patient's anatomy according to an embodiment.

FIG. 5 is a flow diagram illustrating an example method 500 of positioning and securing a portion of the tool 422 shown in FIG. 4 at a target tool location within a patient's anatomy according to an embodiment. As shown at block 502, the method 500 includes positioning the tool 422 (e.g., the sheath 401 of the tool 422) within a portion of an organ, such as the left atrium 303 shown in FIG. 3. As shown at block 504, the method 500 includes rotating the rotatable handle 406 to move (i.e., adjust) the balloon 402 to a target balloon location along the sheath 401. For example, the rotatable handle 406 is rotated (e.g., by a physician) about the screw element 404, causing spring element 403 to expand or contract via wires 407. The expansion of the spring element 403 causes the balloon 402 to move in one direction along the sheath 401 and the contraction of the spring element 403 causes the balloon 402 to move in an opposite direction along the sheath 401.

When the balloon reaches the target balloon location along the sheath 401, rotation of the rotatable handle 406 stops and the balloon 402 is inflated, as shown at block 506. The inflated balloon 502 is then fixed at the target balloon location along the sheath 501 as shown at block 508. The balloon 402 is fixed at the target balloon location, for example, by locking the balloon 402 at the target balloon location using a locking mechanism, such as those described herein. Accordingly, the sheath 401 is prevented from moving from the target tool location to another location within the patient's anatomy (e.g., prevented from slipping out of the left atrium 303). The method 500 described above may be facilitated using ultrasound, fluoroscopic imaging, or other techniques known to those skilled in the art.

Figure 6B:
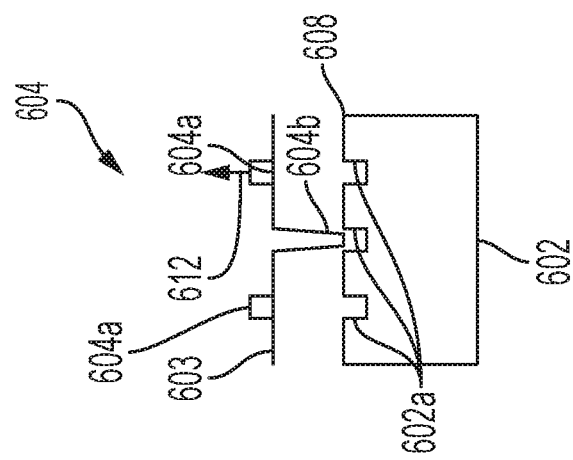
FIG. 6B is an illustration showing examples collapsible protrusions in collapsed positions and engaged positions relative to cavities disposed on an inner side of balloon.
Figure 6A:
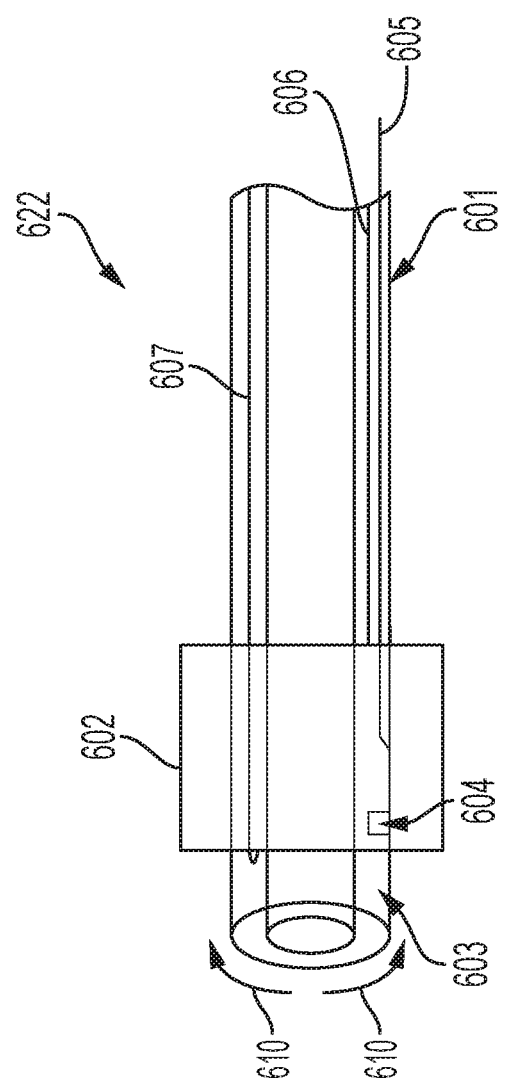
FIG. 6A is a diagram illustrating a portion of an example medical tool having a sheath, a balloon and a collapsible element according to an embodiment.

FIG. 6A is a diagram illustrating components of a tool 622 according to an embodiment. As shown in FIG. 6A, the tool 622 includes a sheath 601 having a sheath wall 603, a balloon 602, a collapsible element 604, a protrusion wire 605, a first balloon wire 606 and a second balloon wire 607.

The first balloon wire and the second balloon wire are string-like elements that can be moved (pulled and released) to facilitate the positioning of the sheath 601 shown in FIG. 6A at a target tool location of a patient (e.g., target location within the left atrium of the heart). The balloon wires 606 and 607 together form a balloon moving mechanism, which are used to adjust the location of the balloon 602 along the length of the sheath's shaft while the protrusion wire 605 is used to fix (e.g., lock) the balloon 602 at a target location along the sheath 601. For example, the first balloon wire 606 may be used to move the balloon 602 in a direction along the sheath 601 from a proximal side of the sheath 601 to a distal side (closer to the tip) of the sheath 601. The second balloon wire 306 may be used to move the balloon 602 in the opposite direction along the sheath 601 from a distal side of the sheath 601 to a proximal side of the sheath 601. The number of balloon wires shown in FIG. 6A is merely exemplary. Balloon moving mechanisms may comprise any number of balloon wires to adjust the location of the balloon 602 along the sheath 601.

FIG. 6B is an illustration showing examples collapsible protrusions in collapsed positions and engaged positions relative to cavities 602a disposed on an inner side 608 of balloon 602. The collapsible protrusions 604a and 604b are examples of a collapsible element 604 shown in FIG. 6A. As shown in FIG. 6B, collapsible protrusions 604a and 604b (e.g., tooth shaped protrusions) disposed on the sheath wall 603. Collapsible protrusions 604a are shown in their collapsed positions. Collapsible protrusion 604b is shown in an engaged (i.e., extended) position. The balloon 602 includes cavities 602a disposed on an inner side 608 of the balloon 602, which engage and disengage from the collapsible protrusions 604a and 604b disposed on the sheath wall 603 to adjust the balloon 602 to different locations along the length of the sheath 601 and prevent (e.g., lock) the balloon 602 from moving along the length of the sheath 601. The number of protrusions 604a and cavities 602a and their locations shown in FIG. 6B is merely exemplary. In another embodiment, cavities disposed on the sheath wall may engage collapsible protrusions disposed on the inner side of the balloon.

For example, when a target location of the balloon is obtained along the proximal-distal direction, the balloon 102 is inflated and the protrusion wire 605 is pulled to cause the protrusions 604a and 604b to move to their engaged positions until the collapsible protrusions 604a and 604b align with and engage the cavities 602a of the balloon 602. When the protrusions 604a and 604b engage with the cavities 602a, the protrusion wire 605 is released and the balloon 602 is fixed at or locked at the target location. The collapsible protrusions 604a and 604b may also be aligned with the cavities 602a by rotating the sheath 601 in the directions shown by the arrows 610 in FIG. 6A.

Figure 7:
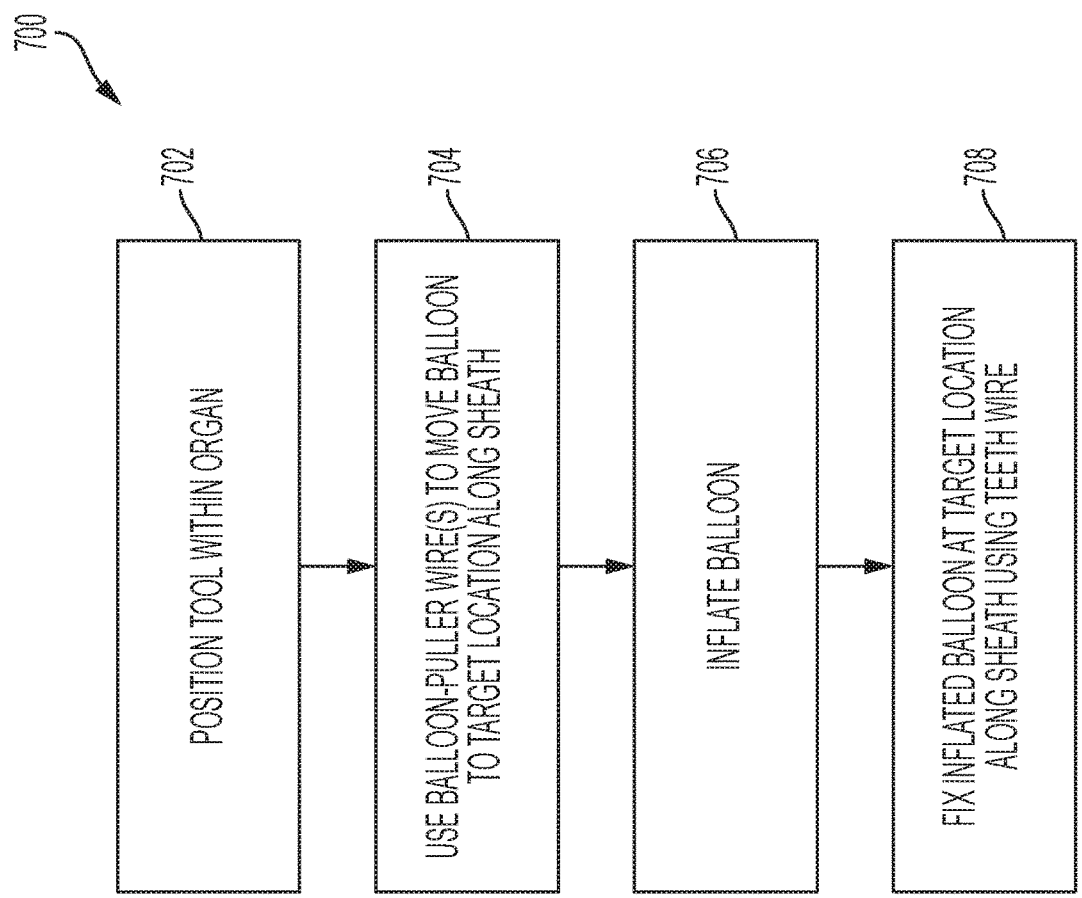
FIG. 7 is a flow diagram illustrating an example method of securing the sheath shown in FIG. 6A at a target location within a patient's anatomy according to an embodiment.

FIG. 7 is a flow diagram illustrating an example method 700 of securing the sheath 601 shown in FIG. 6A at a target tool location within a patient's anatomy according to an embodiment. As shown at block 702, the method 700 includes positioning the sheath 601 within a portion of an organ, such as the left atrium 303 shown in FIG. 3. As shown at block 704, the method 700 includes moving one or both of the balloon wires 606 and 607, which are coupled to the balloon 602, to move (i.e., adjust) the balloon along the sheath 601. For example, balloon wires 606 and 607 may be used to adjust the location of the balloon 602 in opposing directions along the sheath 601.

As shown at block 706, the method 700 includes inflating the balloon 602 when the target balloon location along the sheath 610 is obtained. As shown at block 708, the method 700 includes fixing the balloon 602 at the target location along the sheath 601. For example, the protrusion wire 605 may be pulled until the collapsible element 604 (e.g., one or more collapsible protrusions 604a) are engaged with one or more opposing cavities 602a. When one or more collapsible protrusions 604a are engaged with one or more opposing cavities 602a, the protrusion wire 605 is released and the balloon 602 is fixed (e.g., locked) at the target location on the sheath 601. The method 700 described above may be facilitated using ultrasound, fluoroscopic imaging, or other techniques known to those skilled in the art.

Figure 8A:
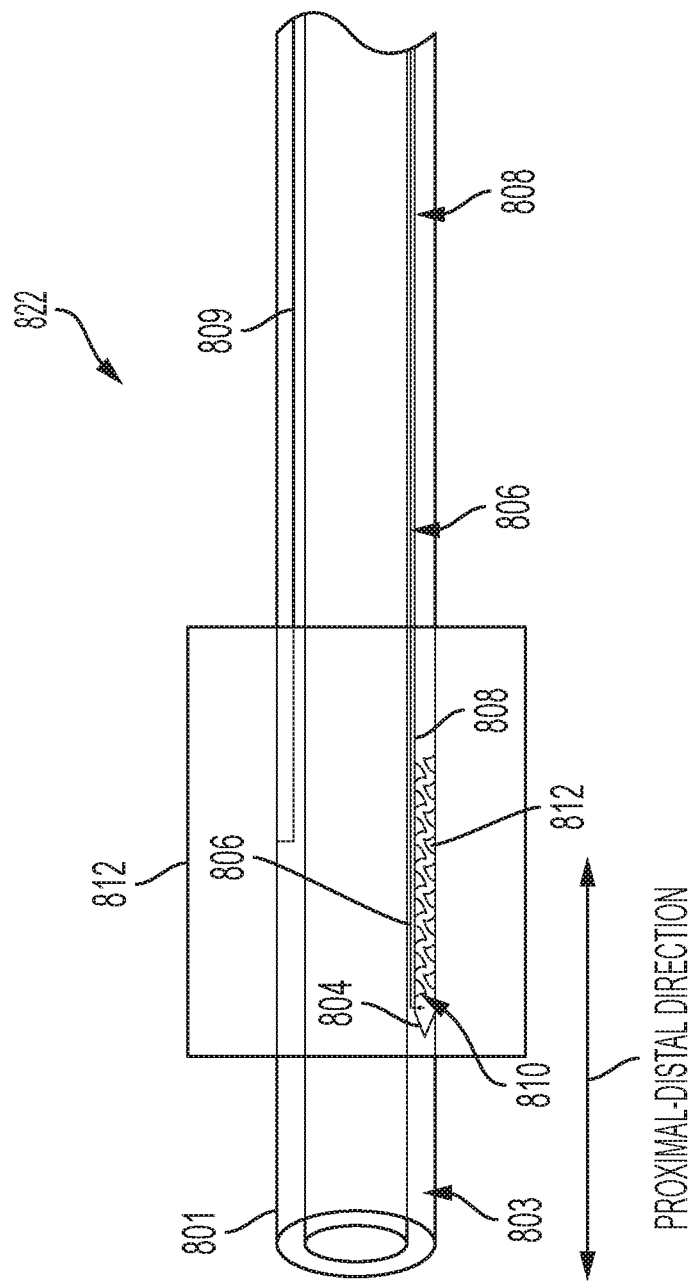
FIG. 8A shows a portion of a tool having a locking mechanism according to an embodiment.

FIG. 8A shows a portion of an example tool 822 having a locking mechanism 804 according to one embodiment. As shown in FIG. 8A, tool 822 includes sheath 801 having a sheath wall 803, an inflatable balloon 802, a locking mechanism wire 806, a first balloon wire 808 and a second balloon wire 809. The sheath 801 includes a scalloped element 810, comprising scalloped protrusions 810a shown in FIGS. 8B and 8C, disposed on the sheath wall 803. The first balloon wire 808 includes a scalloped element 812, comprising scalloped protrusions 812a shown in FIGS. 8B and 8C, opposing the scalloped element 810 disposed on the sheath wall 803. The second balloon wire 809 shown in FIG. 8A does not include a scalloped element. Some embodiments include a second balloon wire 809 having a scalloped element. Embodiments may include any number of balloon wires, including a single balloon wire.

Figure 8B:
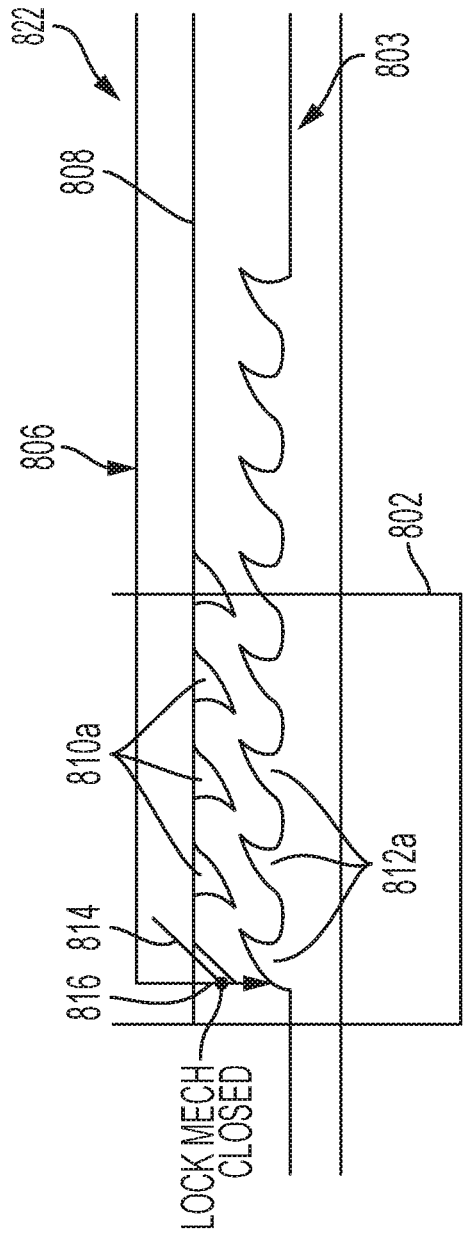
FIG. 8B is a n, cross-sectional view of a portion of the tool shown in FIG. 8A illustrating the locking mechanism in a closed position.
Figure 8C:
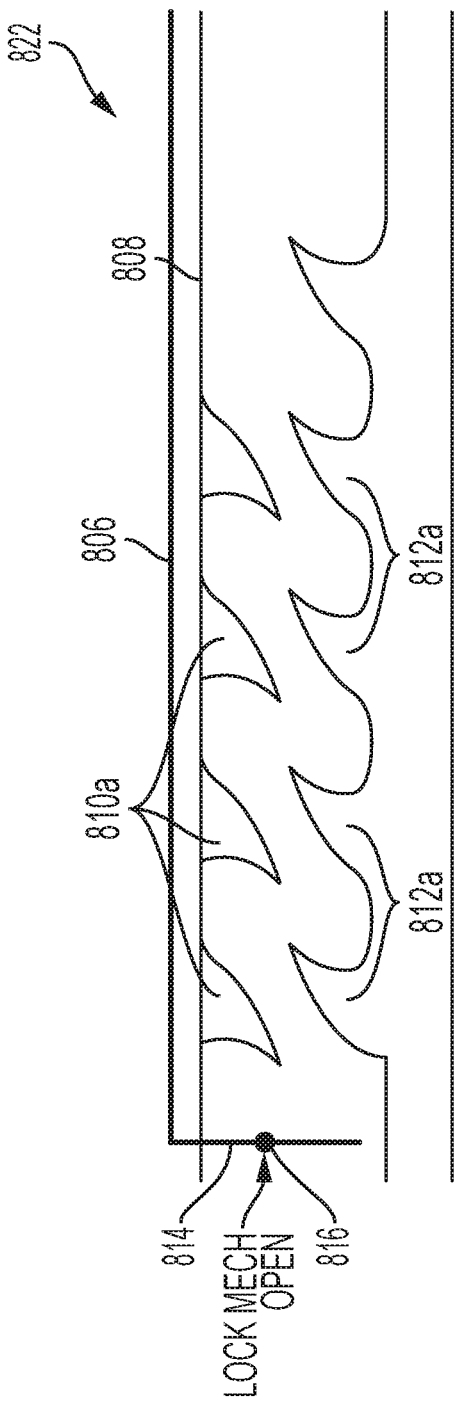
FIG. 8C is an expanded, cross-sectional view of a portion of the tool shown in FIG. 8A illustrating the locking mechanism in an open position.

FIG. 8B is an expanded, cross-sectional view of a portion of the sheath 801 shown in FIG. 8A and the balloon 802 illustrating the locking mechanism 804 in a closed position. FIG. 8C is an expanded, cross-sectional view of a portion of the sheath 801 shown in FIG. 8A and the balloon 802 illustrating the locking mechanism 804 in an open position. The locking mechanism includes a locking mechanism wire 806 and a pivoting arm 814. The pivoting arm is configured to pivot about a pivot point 816. The pivoting arm 814 is coupled to the locking mechanism wire 806 at a pivoting end (via a linkage, which is not shown) and the scalloped protrusions 810a, via the balloon 802, at a balloon end. In the open position shown in FIG. 8C, the scalloped protrusions 812a on the sheath wall 803 are spaced from the opposing scalloped protrusions 810a on the balloon 802. In the closed position shown in FIG. 8B, however, the scalloped protrusions 812a on the sheath wall 803 are moved closer to the opposing scalloped protrusions 810a on the balloon 802. For example, when the locking mechanism wire 806 is moved (pushed or pulled), pivoting arm 814 is caused to pivot about pivot point 816 such that pivoting arm 814 moves between locations shown in FIGS. 8B and 8C and the scalloped protrusions 810a are caused to move between their positions shown in FIGS. 8B and 8C. In addition, unlike the protrusions 604a in the embodiment shown in FIGS. 6A and 6B, the scalloped protrusions 810a and 812a are not collapsible.

Each of the protrusions 810a shown in FIGS. 8A-8C are spaced equally from each other. Each of the protrusions 812a shown in FIGS. 8A-8C are also spaced equally from each other. Embodiments may, however, include unequal spaces between the protrusions. The number and location of the protrusions 810a and 812a shown in FIGS. 8A-8C are exemplary. Embodiments may include any number of protrusions. Similar to FIGS. 6A and 6B, embodiments may include a balloon moving mechanism which comprises any number of balloon wires to adjust the location of the balloon 802 along the sheath 801.

After the tool 822 is positioned at a target location of an organ (e.g., the left atrium 103) of the patient, the first balloon wire 808 is pulled, causing the balloon 802 to move along the sheath in a proximal-distal direction (i.e., in a left-right direction in FIGS. 8A-8C) along the sheath 801. The scalloped protrusions 810a and scalloped protrusions 812a, as shown in their positions in FIG. 8C, are separated from each other such that they are able to move in opposite directions (i.e., left and right directions) without contacting each other, enabling the balloon 802 to move to the target location. When the balloon 802 reaches the target location along the sheath 801, the locking mechanism wire 806 is moved (e.g., pulled), causing the scalloped protrusions 810a and opposing scalloped protrusions 812a to move closer to each other (i.e., in an up-down direction in FIGS. 8A-8C) until the locking mechanism 804 is closed and protrusions 810a and 812a reach their positions shown in FIG. 8B, and fix (e.g., lock) the balloon 802 at the target balloon location along the sheath 801.

Figure 9:
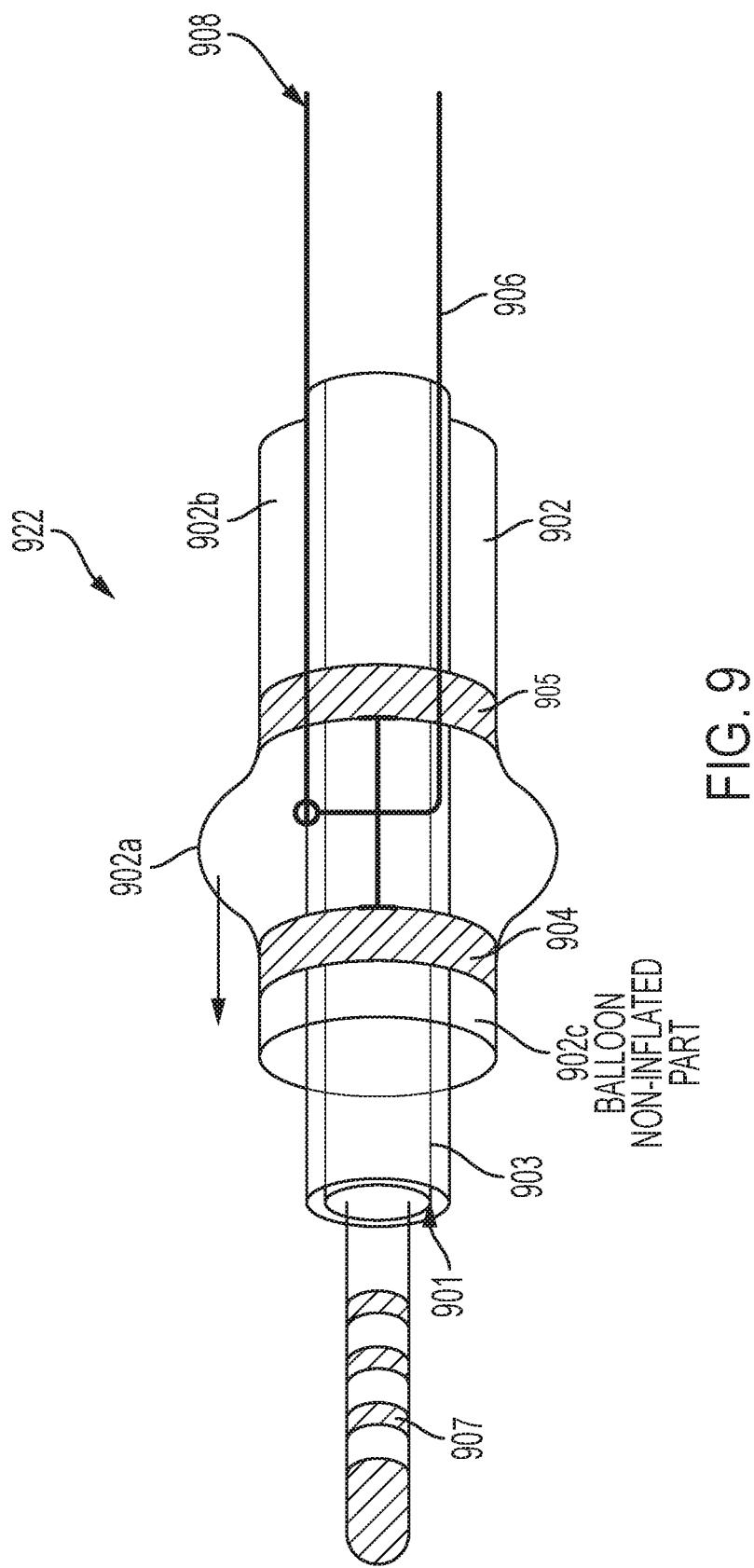
FIG. 9 shows a portion of a tool having a sheath, an inflatable balloon with an inflatable portion and non-inflatable portion and a pair of rings according to an embodiment.

FIG. 9 shows a portion of tool 922 according to an embodiment. As shown in FIG. 9, the tool 922 includes a sheath 901 having a sheath wall 903, a balloon 902 covering a distal part of the sheath 902, a pair of rings 904 and 905, a wire 906 disposed within the sheath wall 903, a catheter 907 and a saline tube 908. The rings 904 and 905 are disposed around the balloon 902 on each side of the balloon 902, are spaced from each other and configured to slide on the balloon 902. The distance between the two rings 904 and 905 is maintained by a fixed element (shown as horizontal bar between the two rings 904 and 905 in FIG. 9), allowing the rings 904 and 905 to move together distally and proximally (left-right directions in FIG. 9) while maintaining an equal distance from each other. The balloon 902 has an inflatable part 902a disposed between the rings 904 and 905 and non-inflatable portions 902b and 902c disposed on opposite side of the rings 904 and 905. The inflatable part 902a is dependent on the saline flow via the saline tube 908. Accordingly, the location and size of the inflatable part 902a of the balloon 902 depends on the location of the rings 904 and 905 which quarantine the saline flow causing the balloon 902 to inflate between the rings 904 and 905. Similar to the embodiments described above, a balloon moving mechanism may comprise any number of balloon wires to adjust the location of the balloon 902 to different locations along the sheath 901. The saline tube 908 enters the balloon 902 between rings 904 and 905 and is attached to the puller wire of the balloon 902 to inflate the inflatable portion 902*a* of the balloon 902 between the rings 904 and 905 with saline.

After the tool 922 is positioned at a target location of an organ (e.g., the left atrium 103) of the patient, the wire 906 is used to move the rings 904 and 905 along the balloon 902 to different locations along the sheath 901. When the balloon is moved, the rings 904 and 905 may slide along the balloon covered distal part of the sheath 901. When the target location of rings 904 and 905 along the balloon 902 is obtained, the balloon 902 is fixed (e.g., locked) into place by inflating the inflatable part 902*a* of the balloon 902, which is the part between rings 904 and 905 depending on the location of the rings 904 and 905 after adjustment.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A medical tool for use in a medical procedure, comprising:
    a sheath having a tube defined by a sheath wall, the sheath extending a length in a proximal-distal direction;
    an inflatable balloon coupled to the sheath;
    a balloon-moving mechanism, coupled to the inflatable balloon, and configured to move the inflatable balloon to different balloon locations along the length of the sheath; and
    a balloon-fixing mechanism comprising at least one collapsible protrusion disposed on one of the sheath and the inflatable balloon, the balloon-fixing mechanism configured to fix the inflatable balloon, when the balloon is inflated, to a target balloon location along the length of the sheath to prevent the medical tool from moving from a target tool location within a portion of an organ of a patient.

2. The medical tool of claim 1,
    the balloon-moving mechanism further comprising at least one balloon wire coupled to the inflatable balloon; and
    the balloon-fixing mechanism further comprising at least one cavity disposed on the other of the sheath and the inflatable balloon,
    wherein movement of the at least one balloon wire causes the inflatable balloon to move along the length of the sheath in the proximal-distal direction, and
    the inflated balloon is fixed at the target balloon location when the at least one collapsible protrusion engages the at least one cavity.

3. The medical tool of claim 2, wherein the inflated balloon is fixed at the target balloon location by pulling a protrusion wire until the at least one collapsible protrusion engages the at least one cavity and releasing the protrusion wire when the at least one collapsible protrusion engages the at least one cavity.

* * * * *